United States Patent [19]

Selman et al.

[11] 4,046,745

[45] Sept. 6, 1977

[54] PREPARATION OF FUNCTIONAL POLYMERS

[75] Inventors: Charles M. Selman; Carl A. Uraneck, both of Bartlesville, Okla.

[73] Assignee: Phillips Petroleum Company, Bartlesville, Okla.

[21] Appl. No.: 690,805

[22] Filed: May 27, 1976

Related U.S. Application Data

[62] Division of Ser. No. 625,743, Oct. 24, 1975, Pat. No. 3,993,853.

[51] Int. Cl.$^2$ .......................... C08F 4/48; C08F 8/00; C08E 8/08
[52] U.S. Cl. .................. 260/77.5 CR; 526/20; 526/21; 526/49; 526/55; 526/175; 526/240
[58] Field of Search ............... 260/77.5 CR; 526/49, 526/55, 175, 20, 21, 240

[56] References Cited

U.S. PATENT DOCUMENTS

| | | | |
|---|---|---|---|
| 2,856,391 | 10/1958 | Diem | 260/94.2 |
| 2,951,831 | 9/1960 | Rernhard | 260/80.7 |
| 3,041,320 | 6/1962 | Chapin et al. | 260/82.1 |
| 3,287,333 | 11/1966 | Zelinski | 260/83.7 |
| 3,294,768 | 12/1966 | Wofford | 260/83.7 |
| 3,317,918 | 5/1967 | Foster et al. | 260/83.7 |
| 3,734,972 | 5/1973 | Noyler et al. | 260/665 |
| 3,801,554 | 4/1974 | Selman | 260/83.7 |
| 3,993,853 | 11/1976 | Selman et al. | 260/77.5 CR X |
| 3,993,854 | 11/1976 | Uraneck et al. | 260/77.5 CR X |

FOREIGN PATENT DOCUMENTS

| | | | |
|---|---|---|---|
| 850,894 | 10/1960 | United Kingdom | 260/94.2 |

OTHER PUBLICATIONS

Journal Polymer Science, vol. 8, pp. 533–543 (1970) by Hsieh "Effect of Lithium Alkoxide on Polymerization".

*Primary Examiner*—William F. Hamrock

[57] ABSTRACT

Lithium salts of monohydroxyalkyl-substituted conjugated alkadienes are employed as comonomers in the polymerization of conjugated dienes, or conjugated dienes with monovinyl aromatic compounds, to produce polymers containing hydroxy functionality. The hydroxy functionality permits efficient curing.

23 Claims, No Drawings

PREPARATION OF FUNCTIONAL POLYMERS

This is a divisional application of Ser. No. 625,743, filed Oct. 24, 1975, now U.S. Pat. No. 3,993,853, patented Nov. 23, 1976.

FIELD OF THE INVENTION

The invention relates to polymers containing hydroxyl functional groups. In another aspect, the invention relates to a process to prepare polymers containing hydroxy functional groups. In a still further aspect, the invention relates to cured polymers.

BACKGROUND OF THE INVENTION

Polymers containing hydroxyl groups in the polymer molecule are particularly useful since such polymers are readily curable with a variety of curing agents, such as the diisocyanates or polyisocyanates. Some hydroxyl functionality heretofore has been provided in polymers by converting the lithium end groups of the living polymer to hydroxyl by treatment with reagents such as the epoxy compounds. However, in polymerizations employing a monolithium initiator, the polymers resulting contain, after hydrolysis, one hydroxyl group per molecule; with a dilithium initiator only two hydroxyl groups per molecule; and so on. Thus, linear polymers, preferred for curing with the types of curing agents mentioned, normally would be expected to contain only up to about 2 hydroxyl groups per polymer molecule. Thus, if the functionality could be increased substantially, i.e., if the polymer molecule could contain more hydroxyl groups per molecule, then greater degrees of functionality would be exhibited, and greater degrees of crosslinking could be obtainable.

BRIEF SUMMARY OF THE INVENTION

We have discovered that polymers with a significantly increased degree of functionality can be prepared by employing as a comonomer a minor amount of lithium salt of a monohydroxy-alkyl-substituted conjugated alkadiene in polymerization with conjugated dienes, or conjugated dienes with monovinyl-substituted aromatic compounds. The resultant polymers contain significantly high levels of hydroxyl groups. The normally liquid or semi-solid polymers so produced by our process can be readily converted into solid products, thus providing an effective means of making a truly castable rubber. The polymers produced in a more normally solid state find effective wide usefulness in foamed stocks such as for insulation.

DETAILED DESCRIPTION OF THE INVENTION

Lithium Salts of Monohydroxyalkyl-substituted Conjugated Alkadienes

Lithium salts of monohydroxyalkyl-substituted conjugated alkadienes are employed by us as comonomers in polymerization with conjugated dienes, or with conjugated dienes plus monovinyl-substituted aromatic compounds, in the preparation of copolymers with increased hydroxyl employing anionic solution polymerization means and a lithium-based initiator.

The lithium salts of hydroxyalkyl-substituted conjugated alkadienes are prepared from hydroxyalkyl-substituted conjugated alkadienes by reaction with either lithium metal or with hydrocarbyllithium compounds.

The monohydroxyalkyl-substituted conjugated alkadienes from which the aforedescribed useful lithium salts are prepared can be represented by:

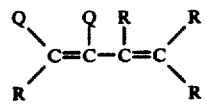

wherein Q represents R, or a hydroxyalkyl group represented by

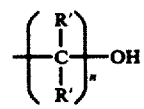

wherein R is hydrogen, or is a hydrocarbon radical which is alkyl, cycloalkyl, aryl, or combination radical such as alkaryl, aralkyl, and the like, and wherein each R can be the same or different. Each R' is individually selected from hydrogen, methyl, or ethyl; and n is a whole number of 1 to 3. The monohydroxyalkyl-substituted conjugated alkadienes contain a single hydroxyalkyl group per molecule. Thus, in each compound, one Q group is R, and one Q group is hydroxyalkyl. There is no specific limitation as far as operability is concerned as to the number of carbon atoms per molecule, though a minimum of 5 carbon atoms is requisite. For general convenience, a carbon atom range of 5 to 12 carbon atoms is suggested, with presently 5 or 6 carbon atoms per molecule being preferred for availability and handling.

Exemplary monohydroxyalkyl-substituted conjugated alkadienes or for shorthand termed alkadienols, are 2,4-pentadien-1-ol, 3,5-hexadien-2-ol, 3-methyl-4,6-decadien-3-ol, 3-cyclohexyl-2,4-pentadien-1-ol, 5-phenyl-2,4-pentadien-1-ol, 6-phenyl-2,4-hexadien-1-ol, 2-p-tolyl-2,4-pentadien-1-ol, 2-methylene-3-butene-1-ol, 2-methyl-3-methylene-4-penten-2-ol, 3-cyclohexyl-2-methylene-3-buten-1-ol, and the like, as well as mixtures thereof. Of these, 2,4-pentadien-1-ol and 2-methylene-3-buten-1-ol presently are the preferred species.

The effective comonomers according to our invention, the lithium salts of the monohydroxyalkyl-substituted conjugated alkadienes, are prepared by contacting the hydroxyalkyl-substituted conjugated alkadienes with lithium metal or with a hydrocarbonlithium compound.

Lithium metal can be employed as wire, ribbon, shot, and the reaction preferably is conducted by contacting the suitable amount of lithium metal with the hydroxyalkyl-substituted conjugated alkadiene in a hydrocarbon solvent, such as pentane, hexane, cyclohexane, or benzene. Presently for exemplary purposes is suggested a range of about 0.95 to 1.05 gram equivalents of lithium per gram mol of alkadienol. Preferred, of course, is a ratio of 1:1, in order to make the desired lithium salt of the hydroxyalkyl-substituted conjugated alkadiene most precisely. However, a slight excess of hydroxyalkyl-substituted conjugated alkadiene is not objectionable; presence of small amounts of unreacted lithium metal are not objectionable since such would be known to initiate polymerization of the desired monomers. However, for maximum employment of our invention, the ratio should be held closely to the suggested range.

Hydrocarbon lithium compounds employed in reacting with the monohydroxyalkyl-substituted conjugated alkadienes include hydrocarbon lithium compounds represented by the formula R(Li)$_x$. R is a hydrocarbon radical which can be saturated aliphatic, saturated cycloaliphatic, aromatic, or combination radical. The integer indicator $x$ has the value of 1 to 4. R, of course, has a valence equal to $x$. While the hydrocarbon radical presently is not limited to size as far as operability is concerned, for convenience and availability the R group will contain 1 to 20 carbon atoms per molecule, and presently 3 to 5 carbon atoms per molecule are preferred because of particularly desirably reactivities.

Exemplary hydrocarbon lithium compounds include methyllithium, isopropyllithium, n-butyllithium, tert-butyllithium, n-decyllithium, phenyllithium, p-tolyllithium, cyclohexyllithium, 1,20-dilithioeicosane, 1,3,5-trilithiopentane, 1,2,4,6-tetralithiocyclohexane and the like. n-Butyllithium is presently preferred because of availability and desirable reactivity.

The amount of hydrocarbyllithium compound employed is the same as described above for lithium metal.

The contacting can be conducted under any conditions suitable to produce lithium salts of the alcohols described. Contacting can be in the alkadienol itself, or the alkadienol can be further diluted with inert hydrocarbon, such as pentane, hexane, cyclohexane, benzene, toluene, etc. Contacting times can be whatever is convenient, from such as less than a minute to 24 hours or more, presently preferred about 15 minutes to 1 hour for satisfactory reaction. Contacting can be conducted at any reaction temperature, under conditions of pressure and temperature suitable to maintain the reactant substantially in the liquid phase. Exemplary temperatures presently suggested are in the range of about 0° to 100° C., presently conveniently about 20° to 50° C.

The desired lithium salts of hydroxyalkyl-substituted conjugated alkadienes can be prepared in a separate reactor, and transferred without isolation of the salt into the polymerization zone; or the desired salt can be prepared directly in the polymerization reactor if desired. It is preferred to exclude oxygen, air, and moisture, since while not objectionable in the preparation of the lithium salt is described, such are objectionable and undesirable, as is known in the art, in polymerization of the monomers described. It should be noted that within the indicated ranges the proportions of lithium or hydrocarbyllithium compound to hydroxyalkyl-substituted alkadiene employed to prepare the corresponding lithium salt of hydroxyalkyl-substituted conjugated alkadiene, the resulting lithium salt of the monohydroxyalkyl-substituted conjugated alkadiene itself has no appreciable initiator properties. Thus, simply contacting the conjugated diene, or conjugated diene and monovinyl-substituted aromatic compound, with the described lithium salt, would not effectively result in polymerization of the monomers.

POLYMERIZATION PROCESS

Thus, it is necessary in order to produce the hydroxy functional polymers according to our invention not only to employ the monomers, conjugated diene, or conjugated diene with monovinyl-substituted aromatic hydrocarbon, plus the lithium salt of hydroxyalkyl-substituted conjugated alkadiene, but further to employ a suitable lithium initiator.

INITIATORS

Suitable lithium hydrocarbon initiators include those represented by the formula R"(Li)$_y$. R" represents a hydrocarbon radical having a valence of $y$. The integer indicator $y$ has the value of from 1 to 4. Presently preferred are the dilithio initiators represented by RLi$_2$ such that the resulting polymer is a linear polymer having two lithium atoms per molecule, one lithium atom at each end of each polymer molecule.

Exemplary species include such as methyllithium, n-butyllithium, phenyllithium, 1,4-dilithiobutane, 1,2-dilithio-1,2-diphenylethane, 1,4-dilithionaphthalene, 1,4-dilithio-2-methylbutane, 1,3,5-trilithiopentane, 1,2,4,8-tetralithioeicosane. It is within the scope of our invention to employ lithium initiators containing more or less than two lithium atoms per molecule. Lithium initiators containing more than two lithium atoms per molecule result in predominantly branched polymer molecules containing a lithium atom at each branch end. Monolithium initiators, of course, produce a polymer molecule with a single lithium atom at one end of the polymer molecule.

MONOMERS

The monomers employed in the process of our invention are conjugated dienes plus the lithium salts of hydroxyalkyl-substituted conjugated alkadienes, or conjugated dienes plus monovinyl-substituted aromatic hydrocarbons plus the lithium salts of hydroxyalkyl-substituted conjugated alkadienes. In any of these polymerization systems, the monomers are employed in admixture one with the other.

Conjugated dienes employed in the process of our invention include any of the conjugated dienes, preferably the hydrocarbon conjugated dienes, known to polymerize with lithium initiators. On an exemplary basis, these conjugated dienes can contain 4 to 12 carbon atoms per molecule, preferably for availability 4 to 8 carbon atoms per molecule, and preferably for industrial purposes those of 4 to 6 carbon atoms per molecule. Exemplary species include such as 1,3-butane, isoprene, piperylene, 2,3-dimethylbutadiene, 1,3-hexadiene, 2,4-octadiene, 5-vinyl-5-decene, 2-phenyl-1,3-butadiene, and the like, alone, in admixture with any two or more, in any desired proportion.

Where desired, the conjugated diene can be polymerized in admixture with one or more monovinyl-substituted aromatic compounds, preferably the hydrocarbon monovinyl-substituted aromatic compounds, known to copolymerize with the polymerizable conjugated dienes in lithium initiated solution-polymerized systems. These monovinyl-substituted aromatic compounds typically contain 8 to 16 carbon atoms per molecule, usually for availability 8 to 12 carbon atoms per molecule, and for commercial preference 8 or 9 carbon atoms per molecule. Exemplary species include styrene, alpha-methylstyrene, m-vinyltoluene, p-tert-butylstyrene, 1-vinylnaphthalene, 4-ethyl-1-vinylnaphthalene, 6-isopropyl-4-methyl-1-vinylnaphthalene, and the like, alone or in admixture.

Preferred proportions are a sufficient amount of conjugated diene as to result in the formation of a substantially rubbery product. For this reason, the amount of conjugated diene component generally should be in the preponderance, such as greater than 50 percent by weight.

The amount of lithium salt of hydroxyalkyl-substituted conjugated alkadiene to employ generally should be in the range of about 1 to 6 parts by weight of total monomers, for the reason that greater than this amount appears to result in an undesirable retardation of the polymerization rate of the primary monomers. Presently preferred is a range of about 2 to 4 parts per 100 parts by weight of total monomers for best results.

The polymerization process itself is conducted under conditions with employment of diluent as known in the art for polymerization of conjugated dienes, or conjugated dienes with monovinyl-substituted aromatic hydrocarbon monomers, employing lithium initiators. Polymerization typically is conducted in a hydrocarbon diluent such as pentane, hexane, cyclohexane, isooctane, benzene, toluene, alone or any admixture thereof, under suitable polymerization temperatures and pressures sufficient to maintain the reactants and diluent substantially in the liquid phase. Any convenient amount of diluent can be employed, such as 100 to 2000 parts by weight per 100 parts by weight of total monomers.

The amount of initiator employed can vary according to the desired molecular weight of the polymer. Generally, the amount employed will be in the range of about 0.5 to 150 milliequivalents of lithium per 100 parts by weight of total polymerizable monomer.

The amount of initiator is exclusive of lithium contained in the hydroxyalkyl-substituted conjugated alkadiene itself. The lithium compound or compounds employed as initiator generally are introduced into the reaction zone after the total monomers are present, and diluent.

Polymerization can be conducted with any polymerization temperature suitable for the monomers to be polymerized. Exemplary temperature range would be about 30° to 100° C., presently preferred about 40° to 60° C. because of reactivity and convenience.

Polymerization times can vary widely depending on monomers, initiator, temperature, and the like, though an exemplary range would be from such as about 0.5 to 15 hours.

At the conclusion of the polymerization reaction, the living polymer containing oxygen-lithium groups from the incorporated lithium salts of conjugated alkadienols and carbon-lithium groups from the polymerization reaction is treated with an agent such as an alkylene oxide to convert the carbon-lithium groups to oxygen-lithium groups. Preferred alkylene oxides include ethylene oxide and propylene oxide. Alkylene oxides generally known in the art can be employed, such as those of 2 to 6 carbon atoms per molecule. Generally from about 1 to 2 and preferably 1.25 to 1.5 moles of alkylene oxide are employed per equivalent of lithium in the initiator.

Said treatment with alkylene oxides is normally carried out after adding from about 2 to about 20 parts by weight per hundred parts by weight total monomers of an ether such as diethyl ether or tetrahydrofuran to maintain a fluid system. Said treatment is carried out for any time and temperature which is necessary to convert substantially all the carbon-lithium groups to oxygen-lithium groups. Usually from 1 minute to 24 hours at temperatures ranging from 30° to 100° C. is sufficient to essentially complete the reaction.

Any convenient means known in the art to isolate the resltant polymers can be employed. It is currently convenient to treat the polymerization system with an alcohol, such as isopropanol, to convert oxygen-lithium groups to hydroxyl groups and to thus fluidize the system. Acidification with aqueous hydrochloric acid followed by washing with water until neutral, addition of any well known stabilizer or antioxidant, and drying, complete the isolation process. Alternately, the polymer cements obtained from the alkylene oxide treatments can be titrated with aqueous hydrochloric acid to the neutral point, filtered to remove lithium chloride and dried to give the desired functional polymer.

The hydroxy-containing polymers prepared as described above can be cured using a number of systems known in the art. They are especially useful in urethane type systems in which a polyisocyanate, preferably a diisocyanate, is mixed with the polymer to convert the polymer hydroxyl groups into urethane-type linkages. If an excess of polyisocyanate is used, a chain extender, such as a polyol, normally is added to convert the excess isocyanate groups into urethane-type linkages. Molding the resulting incompletely cured polymer under heat and pressures completes the conversion of the normally liquid or semi-solid hyroxy-containing polymers into firm, rubbery gumstocks.

Polyisocyanates of general formula $F(NCO)_x$ wherein R is a hydrocarbyl radical of valence $x$ having up to about 20 carbon atoms and wherein $x$ is an integer having the value of from 2 to 4 are useful in the curing of the invention polymers. Examples of commercially available diisocyanates are 2,4-tolylene diisocyanate (TDI), diphenylmethane diisocyanate (MDI), hexamethylene-diisocyanate, and the like. Aryl diiosyanates, such as TDI and MDI, are preferred. Chain extenders are known in the art and are sometimes useful in the curing procedure for the polymers of this invention. Examples of commercially available chain extenders include 1,4-butanediol, 2-ethyl-1,3-hexanediol, trimethylolpropane, triisopropanolamine, N,N-bis(2-hydroxypropyl)aniline, 3,3'-dichlorobenzidine and the like. Especially preferred in the present invention are the diols, such as N,N-bis(2-hydroxypropyl)aniline.

It may sometimes be desirably to include accelerators in the curing system which are well known in the art to accelerate the reaction of isocyanates with hydroxyl groups. Included in such accelerators are dibutyltin dilaurate, stannous octoate, triethylene diamine, etc.

The chain extenders, preferably diols, are normally used in amounts ranging from 0 to 5 and preferably 1 to 3 equivalents of hydroxy per equivalent of polymer hydroxy groups. The polyisocyanates, preferably diisocyanates, are normally employed in amounts ranging from 1 to 1.15 and preferably 1 to 1.05 equivalents of isocyanate per equivalent of total hydroxy (polymer hydroxy plus chain extender hydroxy). Accelerators are usually used in amounts ranging from 0 to 0.5 and preferably 0.15 to 0.25 parts by weight per 100 parts by weight polymer.

Due to the exothermic nature of the isocyanate-hydroxyl reaction it may be desirable or necessary to control the temperature of the mixture during said reaction by means of an external cooling system. It is generally desirable to maintain the temperature of the reacting mixture below about 80° to 100° C. In order to avoid completely curing the polymer prior to introduction of the partially cured mass into the desired mold.

Subsequent molding and complete curing of the polymer can be carried out at any temperature and pressure for any time which results in the desired product. It is currently useful to mold the partially cured polymer at 93° to 121° C. (200° to 250° F.) and 15,000 to 20,000 psig for 1 to 2 hours.

EXAMPLES

Examples given are intended to further illustrate our invention, and for this reason particular species employed, conditions, ratios, should be considered as exemplary and not limitative of the scope of our invention.

EXAMPLE I

Polymers of 1,3-butadiene were prepared using a dilithium initiator, termination of the resulting living polymer with propylene oxide, without the comonomer of our invention.

| RECIPE | | Run 1 | Run 2 |
|---|---|---|---|
| Polymerization | | | |
| Butadiene gm | | 40 | 40 |
| Cyclohexane ml | | 450 | 475 |
| Initiator LIMI-B[a] | | 12 | 12 mmoles |
| Polymerization | Time hrs. | 1.5 | 4 |
| | Temp. °C. | 50 | 50 |
| Termination | | | |
| Tetrahydrofuran ml | | 5 | 5 |
| Propylene Oxide ml | | 7 | 7 |
| Treatment | Time hrs. | 16 | 16 |
| | Temp. °C. | 50 | 50 |

[a]Dilithium initiator prepared in accordance with U.S. Patent 3,287,333, Example I.

To a nitrogen purged reactor pressured to 30 psig with nitrogen were charged the above-stated amounts of cyclohexane, butadiene and initiator, in that order. The reactor was maintained at 50° C. for designated time with constant stirring. The tetrahydrofuran and propylene oxide then were added in that order with vigorous agitation between additions. The reactor was maintained at 50° C. for 16 hours with constant stirring. The polymerization mixture then was fluidized with isopropanol, acidified with aqueous hydrochloric acid, washed with water until neutral, treated with 0.5 parts by weight per one hundred parts by weight total monomers of 2,2'-methylene-bis-(4-methyl-6-t-butylphenol) and heated to steam temperature under a nitrogen stream to remove volatiles.

Table I summarizes the recovered amounts and characterization data of the resultant polymers.

TABLE I

| Run No. | Recovery Gm | % Theory | Visc.[a] | Hydroxyl[b] Wt. % | #/-Molecule | HI[c] | $M_w^{[d]}$ | $M_n^{[d]}$ |
|---|---|---|---|---|---|---|---|---|
| 1 | 49[e] | 106 | 56 | 0.89 | 2.0 | 1.4 | 5300 | 3800 |
| 2 | 46.9 | 100 | 48 | 0.85 | 1.8 | 1.34 | 4900 | 3700 |

[a]Viscosity (poise) at 25.8C. Determined using Brookfield Viscometer, Model RVF, No. 7 spindle.
[b]Wt. % hydroxyl determined as in Anal. Chem. 31, 1808 (1959).
$\#/\text{Molecule} = \frac{M_n \times \text{Wt. \% OH}/100}{17}$
[c]Heterogeneity Index. Calculated as $M_w/M_n$.
[d]Weight average molecular weight and number average molecular weight determined by gel permeation chromatography in accordance with method of Kraus and Stacy, J. Poly. Sci. A-2, 657 (1972).
[e]Possibly not dry.

As was expected, the polymers resulting from capping the living polymer of butadiene initiated with dilithium initiator with propylene oxide contained approximately two hydroxyl groups per molecule.

EXAMPLE II

Polymers were prepared employing the lithium salt of 2,4-pentadien-1-ol as a comonomer with butadiene in the preparation of polymers according to our invention. A dilithium initiator was employed, and the living polymers were terminated with propylene oxide, so as to provide comparison with the polymers of Example I.

| Recipe and Charge Order | | |
|---|---|---|
| Cyclohexane | 475 | |
| 2,4-Pentadien-1-ol | var. | position in charge order also variable |
| n-Butyllithium | var. | |
| Butadiene gm | 40 | |
| LIMI-B mmoles | 12 | |
| Polymerization Time hrs. | 4 | |
| Temp. °C. | 50 | |
| Termination | | |
| Tetrahydrofuran ml | 5 | |
| Propylene oxide ml | 7 | |
| Termination Time hrs. | 16 | |
| Temp. °C. | 50 | |

Table II shows the polymerization recipe variable.

TABLE II

| Run No. | PDO[a] mmoles | NBL[b] mmoles | Salt Prep. | Order in Charge |
|---|---|---|---|---|
| 3 | 18 | 18 | in situ[c] | c |
| 4 | 12 | 12 | in situ[c] | c |
| 5 | 12 | 12 | Preform[d] | d |
| 6 | 6 | 6 | Preform[d] | d |

[a]2,4-Pentadien-1-ol
[b]n-Butyllithium
[c]PDO and NBL mixed in reactor in cyclohexane. Contact time was 30 minutes at 30° C. before proceeding with charging.

For Runs 3 and 4 a nitrogen purged reactor was pressured to 30 psig with nitrogen. Amounts of cyclohexane, PDO and NBL as given in the Recipe and Table II were charged in that order after which contact time of 30 minutes at 30° C. was allowed. After addition of butadiene and initiator in that order the reactor was maintained at 50° C. for 4 hours. Addition of THF and PO in amounts given in the recipe in that order with agitation between additions followed by continued heating at 50° C. for 16 hours and workup as described in Example I gave polymers the recovered amounts and characterization data of which are recorded in Table III.

TABLE III

| Run No. | Recovery Gm | % Conv | Visc | Hydroxyl Wt. % | #/molecule | HI | $M_w$ | $M_n$ |
|---|---|---|---|---|---|---|---|---|
| 3 | 46.2 | 100 | 348 | 0.96 | 4.2 | 1.46 | 11000 | 7500 |
| 4 | 47.1 | 100 | 184 | 0.96 | 3.0 | 1.6 | 8500 | 5300 |
| 5 | a | — | 136 | 1.00 | 2.8 | 1.51 | 7600 | 4800 |
| 6 | 46.6 | 100 | 88 | 0.99 | 2.5 | 1.5 | 6400 | 4300 | a)Not determined.

The data in Table III indicate that the recovered polymers have more hydroxyl groups per molecule than observed in the control runs of Example I. Thus, it is concluded that the lithium salt of 2,4-pentadien-1-ol was incorporated as a comonomer in the polymer. This conclusion is further verified by the observation that hydroxyls/molecule values increased with increasing amount of the original salt.

It should be further noted that increasing salt content resulted in increased molecular weight of the resultant polymers, possibly indicating that the salt serves as a slow polymerization terminator, i.e., a slow poison.

EXAMPLE III

The following invention runs (7 and 8) and comparative run (9) were conducted generally as described in Examples II and I, respectively, with the only differences as noted below.

| Recipe | |
| --- | --- |
| Cyclohexane ml | 450 |
| 2,4-Pentadien-1-ol mmoles | var. |
| n-Butyllithium mmoles | var. |
| (PDO and NBL contacted in the cyclohexane 30 minutes at 30° C. before proceeding) | |
| Butadiene gm | 40 |
| LIMI-B mmoles | 12 |
| Tetrahydrofuran ml | 2 |
| Polymerization time | variable |
| temp. ° C. | 50 |
| Termination | |
| Propylene oxide ml | 7 |
| Time Hrs. | 16 |
| Temp. ° C. | 50 |

Table IV gives the polymerization variables.

TABLE IV

| Run No. | PDO mmoles | NBL mmoles | Pzn Time Hrs. |
| --- | --- | --- | --- |
| 7 | 12 | 12 | 1.5 |
| 8 | 12 | 12 | 2.5 |
| 9 | 0 | 0 | 1.5 |

Other than changes in amounts of cyclohexane and tetrahydrofuran and polymerization time, the only other difference between Runs 7 and 8 and Run 4 was the introduction of THF prior to the polymerization step in the former and after the polymerization step in the latter. Likewise the only difference between comparative Run 9 and comparative Run 1 was the use of a smaller amount (2 ml) of THF introduced before the polymerization step in the former compared to the larger amount of THF (5 ml) introduced after the polymerization step of the latter.

Recovery and characterization data given in Table V show that adding THF prior to the polymerization step and in smaller amounts had little effect on the resultant polymers. Comparison of inventive Runs 7 and 8 with comparative Run 9 leads to the same conclusions as mentioned above in Example II.

TABLE V

| Run No. | Recovery Gm | % | Visc. | Hydroxyl Wt. % | #/molecule | HI | $M_w$ | $M_n$ |
| --- | --- | --- | --- | --- | --- | --- | --- | --- |
| 7 | 45 | 97.5 | 300 | 0.97 | 3.0 | 1.51 | 8000 | 5300 |
| 8 | 46.1 | 100 | 268 | 0.99 | 3.1 | 1.44 | 7600 | 5300 |
| 9 | 45.9 | 99 | 84 | 0.73 | 1.6 | 1.30 | 4900 | 3800 |

EXAMPLE IV

The following Run 10 illustrates the use of the lithium salt of 2-methylene-3-buten-1-ol as a comonomer with butadiene in the preparation of polymers using a dilithium initiator and termination of the resultant living polymers with propylene oxide.

| Recipe and Charge Order | |
| --- | --- |
| Cyclohexane ml | 200 |
| 2-methylene-3-buten-1-ol (MBO) | var |
| n-Butyllithium | var |
| (2-methylene-3-buten-1-ol and NBL contacted 30 minutes at 30° C. in cyclohexane before proceeding) | |
| Butadiene gm | 20 |
| LIMI-B mmoles | 6.45 |
| Polymerization Time hrs. | 2 |
| Temp. ° C. | 50 |
| Termination | |
| Tetrahydrofuran ml | 5 |
| Propylene oxide ml | 5 |
| Termination Time hrs. | 16 |
| Temp. ° C. | 50 |

Table VII shows the polymerization variables.

TABLE VI

| Run No. | MBO mmoles | NBL mmoles |
| --- | --- | --- |
| 10 | 0 | 0 |
| 11 | 18 | 18 |
| 12 | 12 | 12 |
| 13 | 6 | 6 |

For Runs 11, 12 and 13 a nitrogen purged reactor was pressured to 30 psig with nitrogen and charged with the above stated amounts of cyclohexane, 2-methylene-3-buten-1-ol, and n-butyllithium in that order. After 30 minutes contact time at 30° C., the butadiene and initiator were added and the continuously stirred polymerization mixture was heated to 50° C. for 2 hours. Introduction of THF and PO, and continued heating at 50° C. for 16 hours and workup as described in Example I, gave the inventive polymers described in Table VII.

Comparative Run 10 was conducted as described for invention Runs 11, 12 and 13 with the only difference being omission of 2-methylene-3-buten-1-ol and n-butyllithium.

TABLE VII

| Run No. | Recovery gm | % | Visc. | Hydroxyl Wt.% | #/molecule | HI | $M_w$ | $M_n$ |
| --- | --- | --- | --- | --- | --- | --- | --- | --- |
| 10 | 22.3 | 100 | 35 | 0.85 | 1.5 | 1.25 | 3900 | 3100 |
| 11 | 23.2 | 100 | a | 1.06 | 4.8 | 2.2 | 16500 | 7700 |
| 12 | 22.2 | 100 | 126 | 1.01 | 2.6 | 1.56 | 6700 | 4300 |
| 13 | 22.8 | 100 | 58 | 0.81 | 1.6 | 1.34 | 4600 | 3400 | a Too high to determine using procedure described in footnote of Table II.

The data in Table VII indicate that the lithium salt of 2-methylene-3-buten-1-ol was incorporated as a comonomer with butadiene. Like those discussed in Example II, these data likewise suggest that the lithium salt may be functioning as a slow poison.

EXAMPLE V

The following Runs illustrate the curing of some of the above described polymers using a urethane-type curing system.

| Recipe | Amount |
| --- | --- |
| Polymer | Var. |
| Dibutyltin dilaurate (DBTDL) | Var. |
| Isonate 143L<sup>c</sup> | Var. |

| Recipe | Amount |
| --- | --- |
| -continued | |
| N,N-bis(2-hydroxypropyl)aniline[b] | Var. |

[a]A liquid diisocyanate marketed by The Upjohn Company which is structurally similar to diphenylmethane diisocyanate.
[b]Marketed by The Upjohn Company as Isonal C-100.

Table VIII shows the amounts of components and the mix conditions.

TABLE VIII

| Run No. | Polymer | | | DBTDL gm | Diisocyanate | | | Diol | | |
| --- | --- | --- | --- | --- | --- | --- | --- | --- | --- | --- |
| | Run No. | Gm | OH[a] | | mmole | Min | Temp* | mmole | Min | Temp* |
| 14 | 1 | 18 | } 17.5 | 0.079 | 85 | 30 | 41 | 67.5 | 1 | 68 |
| | 2 | 17 | | | | | | | | |
| 15 | 2 | 17 | | | | | | | | |
| | 4 | 25 | } 20.2 | 0.079 | 85 | 45 | 54 | 64.8 | 0.5 | 70+ |
| 16 | 5 | 10 | | | | | | | | |
| | 4 | 8 | } 16 | 0.036 | 58 | 45 | 52 | 42.5 | 0.5 | 67 |
| 17 | 5 | 15 | | | | | | | | |
| | 7 | 18 | } 19.6 | 0.079 | 85 | 45 | 69 | 65.4 | 0.5 | 90 |
| | 8 | 17 | | | | | | | | |

[a]Millimoles of hydroxyl contained in the particular amount of polymer used.
*Final temperature in ° C of mixture at end of specified time.

The polymers to be cured were degassed at 105° to 110° C for 0.5 hour at 8 to 10 torr. After cooling to 36° C the vacuum was relieved with dry nitrogen. The DBTDL was mixed into the polymer and degassing at 30° to 35° C and 50 torr vacuum was resumed. A temperature increase was observed as noted in Table VIII as the exothermic reaction occurred for the specified time interval between the diisocyanate and the polymer hydroxyls. After the exothermic reaction of the polymer hydroxyls with the dissocyanate subsided and the specified time was achieved the chain extender (diol) was added and 50 torr vacuum was resumed. A very rapid temperature increase was observed such that after about 0.5 to 1 minute the temperatures recorded in Table VIII were reached. The reactor then was opened to the air and the partially cured polymer was placed in a mold. Molding the polymer at 107° C (225° F) for 1.5 hr at 16,000 psig gave firm gumstocks, the characterization data of which are given in Table IX.

TABLE IX

| Run No. | Gel %[a] | Swell[a] Index | Tensile[b], psig | Elong.[b] % | 300%[b] Modulus psig | Shore A[c] Hardness | Tear[d] pi |
| --- | --- | --- | --- | --- | --- | --- | --- |
| 14 | 88 | 15 | 1270 | 300 | 1240 | 59 | 110 |
| 15 | 66 | 16 | 1210 | 125 | — | 68 | 110 |
| 16 | 78 | 9 | 830 | 125 | — | 69 | 125 |
| 17 | 65 | 17 | 430 | 120 | — | 47 | 40 |

[a]Determined as described in U.S. Pat. 3,135,716 Col. 16.
[b]ASTM D-412-66
[c]ASTM D-2240-68
[d]ASTM D-624-54, Die A.

The gumstocks obtained from inventive Runs 15, 16, and 17 showed some signs of inhomogeneity, such as sticky spots and opacity, possibly due to inadequate mixing of the diol into the isocyanate-reacted polymer possibly resulting from the rapid, exothermic reaction with the chain extender which rapidly increased the viscosity of the polymer mixture. While the cured invention polymers of Runs 15, 16, and 17, do not show improved properties over those of comparative Run 14 under the curing conditions employed, it is our opinion that more carefully controlled curing conditions would show an effect attributable to the increased functionality (hydroxy content) of the invention polymers. The shorter elongation, and the higher Shore A hardness, however, both indicate a tighter cure which is indicative of the presence of a greater functionality, e.g., greater number of hydroxyl groups per polymer molecule.

The disclosure, including the data, illustrate the value and effectiveness of our invention. The examples, the knowledge and background of the field of the invention and general principles of chemistry and other applicable sciences have formed the bases from which the broad descriptions of the invention, including the ranges of conditions and generic groups of operating have been developed, which have formed, in turn, the bases for our claims here appended.

We claim:

1. A process for preparing a cured polymer which comprises the steps of:
   a. copolymerizing at least one conjugated diene, or at least one conjugated diene with at least one monovinyl-substituted aromatic hydrocarbon, with a minor effective amount for a lithium salt of a monohydroxyalkyl-substituted conjugated alkadiene as comonomer, under solution polymerization conditions of temperature and pressure and employing an effective amount of a lithium-based initiator, thereby preparing a copolymer, wherein said lithium salt of a monohydroxyalkyl-substituted conjugated alkadiene represents the reaction product of a monohydroxyalkyl-substituted conjugated alkadiene with lithium or with a hydrocarbyllithium compound, and wherein said monohydroxyalkyl-substituted conjugated alkadiene is represented by the formula

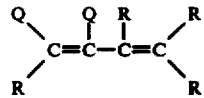

wherein Q is R or a mononydroxyalkyl group represented by

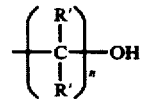

wherein each R is hydrogen or is an alkyl, cycloalkyl, aryl, or combination radical; each R' is hydrogen, methyl, or ethyl; n is an integer of 1 to 3; such that said monohydroxyalkyl-substituted conjugated alkadiene contains 1 hydroxyalkyl group per molecule;

b. treating said copolymer from said step (a) with an effective amount of an alkylene oxide; and c. curing the alkylene oxide-treated copolymer with a polyisocyanate curing system.

2. The process according to claim 1 wherein said monohydroxyalkyl-substituted conjugated alkadiene contains 5 to 12 carbon atoms per molecule.

3. The process according to claim 2 whereinsaid monohydroxyalkyl-substituted conjugated alkadiene is 2,4-pentadien-1-ol, 3,5-hexadien-2-ol, 3-methyl-4,6-decadien-3-ol, 3-cyclohexyl-2,4-pentadien-1-ol, 5-phenyl-2,4-pentadien-1-ol, 6-phenyl-2,4-hexadien-1-ol, 2-p-tolyl-2,4-pentadien-1-ol, 2-methylene-3-buten-1-ol, 2-methyl-3-methylene-4-penten-2-ol, 3-cyclohexyl-2-methylene-3-buten-1-ol, or mixture thereof.

4. The process according to claim 1 wherein said lithium or hydrocarbyllithium compound employed in reaction with said monohydroxyalkyl-substituted conjugated alkadiene is said hydrocarbyllithium compound and is represented by $R(Li)_x$ wherein R is a hydrocarbon radical which is saturated aliphatic, saturated cycloaliphatic, or aromatic, and $x$ is an integer of 1 to 4, such that R has a valence equal to $x$ and contains 1 to 20 carbon atoms per R group.

5. The process according to claim 4 wherein said hydrocarbyllithium compound is methyllithium, isopropyllithium, n-butyllithium, tert-butyllithium, n-decyllithium, phenyllithium, p-tolyllithium, cyclohexyllithium, 1,20-dilithioeicosane, 1,3,5-trilithiopentane, or 1,2,4,6-tetralithiocyclohexane.

6. The process according to claim 5 employing a ratio of said hydrocarbyllithium compound $R(Li)_x$ to said monohydroxyalkyl-substituted conjugated alkadiene in the range of about 0.95 to 1.05 gram equivalents of lithium per gram mol of alkadienol, and wherein said reaction product is prepared by contacting said hydrocarbyllithium compound and said monohydroxyalkyl-substituted conjugated alkadiene at a temperature of about 0° to 100° C. employing a hydrocarbon diluent.

7. The process according to claim 1 employing about 1 to 6 parts by weight lithium salt of a monohydroxyalkyl-substituted conjugated alkadiene per 100 parts by weight total monomers.

8. The process according to claim 7 wherein said range is about 2 to 4 parts by weight per 100 parts by weight of total monomers.

9. The process according to claim 8 employing a proportion of said conjugated diene monomer in the range of about 50 to 100 parts by weight of total monomer excluding said lithium salt of a monohydroxyalkyl-substituted conjugated alkadiene comonomer, and wherein said conjugated diene contains 4 to 12 carbon atoms per molecule.

10. The process according to claim 9 wherein said polymerization is a copolymerization of a conjugated diene with a monovinyl-substituted aromatic compound, wherein said conjugated diene contains 4 to 12 carbon atoms per molecule, and said monovinyl-substituted aromatic compound contains 8 to 16 carbon atoms per molecule.

11. The process according to claim 10 wherein said monovinyl-substituted aromatic hydrocarbon compound is styrene, alpha-methylstyrene, m-vinyltoluene, p-tert-butylstyrene, 1-vinylnaphthalene, 4-ethyl-1-vinylnaphthalene, or 6-isopropyl-4-methyl-1-vinylnaphthalene.

12. The process according to claim 9 wherein said conjugated diene is 1,3-butadiene, isoprene, piperylene, 2,3-dimethylbutadiene, 1,3-hexadiene, 2,4-octadiene, 5-vinyl-5-decene, 2-phenyl-1,3-butadiene.

13. The process according to claim 9 wherein said lithium-based initiator is a hydrocarbyllithium compound represented by $R''(Li)_y$ wherein R'' is a hydrocarbon radical having a valence of $y$, and $y$ is an integer of 1 to 4.

14. The process according to claim 13 wherein said lithium initiator is methyllithium, n-butyllithium, phenyllithium, 1,4-dilithiobutane, 1,2-dilithio-1,2-diphenylethane, 1,4-dilithionaphthalene, 1,4-dilithio-2-methylbutane, 1,3,5-trilithiopentane, or 1,2,4,8-tetralithioeicosane.

15. A process according to claim 13 wherein said polymerization conditions include polymerization in a hydrocarbon diluent, employing said lithium initiator in the range of about 0.5 to 150 milliequivalents of lithium per 100 parts by weight of total polymerizable monomer, excluding lithium derived from said lithium salt of a monohydroxyalkyl-substituted conjugated alkadiene, and employing a polymerization temperature in the range of about 30° to 100° C.

16. The process according to claim 15 wherein said copolymer resulting from substantial completion of polymerization of said monomers contains oxygen-lithium and carbon-lithium groups, said treatment of said copolymer with said alkylene oxide is effective to convert carbon-lithium groups to oxygen-lithium groups, and said step (b) is followed by termination with a reagent effective to convert said oxygen-lithium groups to hydroxy groups.

17. The process according to claim 16 wherein said alkylene oxide contains 2 to 6 carbon atoms per molecule, and is employed in a range of about 1 to 2 moles of alkylene oxide per equivalent of lithium in the initiator employed in said polymerization, and wherein said treatment with said alkylene oxide is carried out in a hydrocarbon diluent in admixture with an ether in an amount effective to maintain a substantially fluid system, and said treatment is carried out at a temperature of about 30° to 100° C. for a time effective for conversion of said carbon-lithium groups.

18. The process according to claim 17 wherein said polyisocyanate is represented by $R'''(NCO)_z$ wherein R''' is a hydrocarbon radical of a valence of $z$ having up to about 20 carbon atoms per molecule, where $z$ is an integer having a value of 2 to 4.

19. The process according to claim 18 wherein said alkylene oxide is ethylene oxide or propylene oxide.

20. The process according to claim 19 wherein said polyisocyanate is 2,4-tolylenediisocyanate, diphenylmethane, diisocyanate, or hexamethylene diisocyanate.

21. The process according to claim 20 wherein said treatment with said polyisocyanate is conducted in the further presence of a chain extender 1,4-butanediol, 2-ethyl-1,3-hexanediol, trimethylolpropane, triisopropanolamine, N,N-bis(2-hydroxypropyl)aniline, or 3,3'-dichlorobenzidene.

22. The process according to claim 21 wherein said polyisocyanate is employed in a ratio of about 1 to 1.15 equivalents of isocyanate per equivalent of total hydroxy copolymer.

23. The cured polymer prepared by the process of claim 1.

* * * * *